United States Patent [19]

Prescott

[11] Patent Number: 5,554,188
[45] Date of Patent: Sep. 10, 1996

[54] UNIVERSAL MIDDLE EAR PROSTHESIS

[75] Inventor: Anthony Prescott, Arlington, Tenn.

[73] Assignee: XOMED, Inc., Jacksonville, Fla.

[21] Appl. No.: 419,833

[22] Filed: Apr. 11, 1995

Related U.S. Application Data

[63] Continuation of Ser. No. 55,181, Apr. 29, 1993, abandoned.

[51] Int. Cl.$^6$ ................................................ A61F 2/18
[52] U.S. Cl. ............................................................ 623/10
[58] Field of Search ......................... 623/10, 11, 16, 623/66; 181/126, 130, 134, 135

[56] References Cited

U.S. PATENT DOCUMENTS

| | | | |
|---|---|---|---|
| 4,052,754 | 10/1977 | Homsy | 3/1.9 |
| 4,131,597 | 12/1978 | Bluethgen et al. | 260/42.18 |
| 4,349,470 | 9/1982 | Battista | 260/117 |
| 4,386,179 | 5/1983 | Sterling | 524/269 |
| 4,481,323 | 11/1984 | Sterling | 524/269 |
| 4,511,354 | 4/1985 | Sterling | 604/98 |
| 4,548,959 | 10/1985 | Nagai et al. | 523/115 |
| 4,563,486 | 1/1986 | Nemcek et al. | 523/115 |
| 4,601,723 | 7/1986 | McGrew | 623/10 |
| 4,613,640 | 9/1986 | Deisler et al. | 524/264 |
| 4,623,553 | 11/1986 | Ries et al. | 427/2 |
| 4,655,776 | 4/1987 | Lesinski | 623/10 |
| 4,659,617 | 4/1987 | Fujii et al. | 428/221 |
| 4,713,077 | 12/1987 | Small | 623/16 |
| 4,722,948 | 2/1988 | Sanderson | 523/115 |
| 4,728,327 | 3/1988 | Gersdorft | 623/10 |
| 4,740,209 | 4/1988 | Gersdorff | 623/10 |
| 4,744,792 | 5/1988 | Sander et al. | 623/10 |
| 4,776,890 | 10/1988 | Chu | 106/161 |
| 4,849,285 | 7/1989 | Dillon | 428/330 |
| 4,859,383 | 8/1989 | Dillon | 264/43 |
| 4,863,472 | 9/1989 | Tormala et al. | 623/16 |
| 4,944,750 | 7/1990 | Cox, Jr. | 623/8 |
| 4,968,317 | 11/1990 | Tormala et al. | 606/77 |
| 4,976,736 | 12/1990 | White et al. | 623/16 |
| 5,061,280 | 10/1991 | Prescott | 623/10 |
| 5,067,965 | 11/1991 | Ersek et al. | 623/66 |
| 5,084,051 | 1/1992 | Tormala et al. | 606/77 |
| 5,116,371 | 5/1992 | Christensen et al. | 623/11 |

FOREIGN PATENT DOCUMENTS

| | | | |
|---|---|---|---|
| 58-61744 | 4/1983 | Japan . | |
| 2041759 | 9/1980 | United Kingdom | 623/10 |

OTHER PUBLICATIONS

*Biomaterials* by L.Ll Henck, May 23, 1980.

Primary Examiner—Debra S. Brittingham
Attorney, Agent, or Firm—John S. Hale; Gipple & Hale

[57] ABSTRACT

A middle ear prosthesis 10 is provided having a first portion 12 including a head 16 for engaging the tympanic membrane and a cannulated shaft 20 extending from head 16. The first portion of 12 is operable alone as a partial ossicular prosthesis. A second portion 14 is provided including a shaft having a distal portion 26 insertable in the cannulated shaft 20 of first portion 12. Second portion 14 when in combination with first portion 12 provides a total ossicular prosthesis.

13 Claims, 1 Drawing Sheet

UNIVERSAL MIDDLE EAR PROSTHESIS

CROSS REFERENCE TO RELATED APPLICATIONS

This application is a continuation of application Ser. No. 08/055,181 filed Apr. 29, 1993, entitled "Universal Middle Ear Prosthesis" by Anthony D. Prescott, now abandoned.

TECHNICAL FIELD OF THE INVENTION

The present invention relates in general to medical prostheses and in particular to a universal middle ear prosthesis.

BACKGROUND OF THE INVENTION

The middle ear is an air-filled space which contains three auditory ossicles providing mechanical linkage between the tympanic membrane or ear drum and the opening to the inner ear, commonly referred to as the "oval window." The three auditory ossicles are the malleus, the incus and the stapes. The malleus includes a handle portion and a head portion, the handle portion contacting the tympanic membrane. The stapes includes an arch, formed by a pair of limbs, and a footplate. The footplate communicates with the oval window leading to the inner ear. The incus couples vibrations from the head portion of the malleus, when the malleus handle vibrates in response to sound impinging on the tympanic membrane, to the arch of the stapes. The stapes footplate in turn communicates these auditory vibrations to the inner ear. The leaver action of the ossicles within the middle ear causes amplification of the sound vibrations with the result that greater vibrational force is experienced at the oval window than at the tympanic membrane.

Ossicular prostheses are implantable medical devices used to replace these middle ear structures when they become damaged. Presently, two conventional types of ossicular prostheses are available to hospitals for middle ear ossicular reconstruction. Total prostheses are designed to replace the malleus, incus and superstructure of the stapes while partial prostheses are designed to replace the malleus and the incus only. Presently, hospitals must stock both the total and partial prosthesis versions such that they can provide for all contingencies. In addition to having to stock two different types of prostheses, hospitals are typically required to stock multiples of each prosthesis in the event that one of a particular type is accidentally dropped or broken. In sum, hospitals carry a substantial burden in having to maintain stocks of both total and ossicular prostheses.

Thus, the need has arisen for an ossicular prosthesis which allows hospitals to significantly reduce their stocking burdens. Importantly, such a prosthesis should allow for flexibility without sacrificing the functionality provided by both the presently available total and partial prostheses.

SUMMARY OF THE INVENTION

According to the invention, a middle ear prosthesis is provided which includes a first portion having a head for engaging the tympanic membrane and a cannulated shaft extending from the head. The first portion is operable alone as a partial ossicular prosthesis. A second portion is provided including a shaft with a distal portion insertable in the cannulated shaft of the first portion. The second portion when in inserted combination with the first portion provides a total ossicular prosthesis.

The present invention overcomes many of the stocking problems currently experienced by hospitals. Instead of stocking two different sets of complete prostheses, hospitals may now stock the individual parts and use these parts only as required for a total or partial ossicular replacement. Further, when a portion of a universal prosthesis according to the invention is dropped or broken, only that part needs to be replaced rather than an entire prosthesis. In sum, the present invention provides hospitals with substantially increased flexibility without sacrificing the functionality currently provided by both total and partial prostheses.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
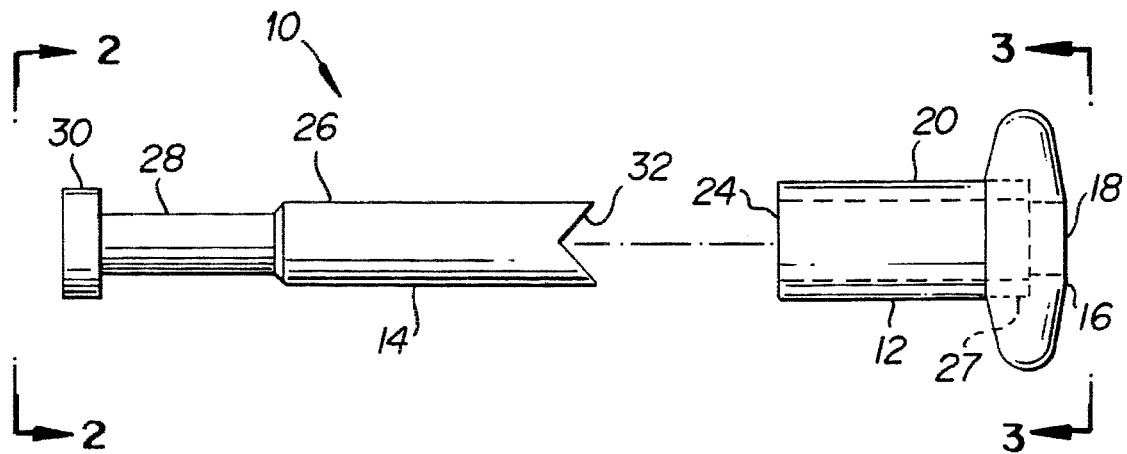
FIG. 1 is a mechanical schematic drawing of an illustrative universal middle ear prosthesis embodying the principles of the present invention.
Figure 2:
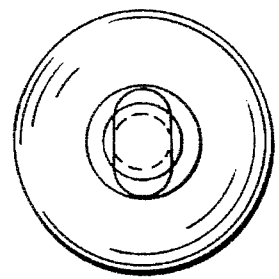
FIG. 2 is an end view of the prosthesis depicted in FIG. 1 as viewed from line 2—2.
Figure 3:
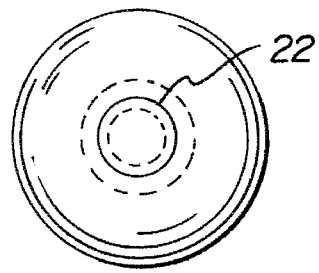
FIG. 3 is an end view of the prosthesis depicted in FIG. 1 as viewed from line 3—3.

The preferred embodiment of the present invention and its advantages are best understood by referring to FIGS. 1–3 of the drawings, like numerals being used for like and corresponding parts of the various drawings.

FIG. 1 is a mechanical schematic diagram of a universal middle ear prosthesis 10 embodying the principles of the present invention. Universal prostheses 10 is a two part device which includes a "partial" prosthesis portion 12 and a corresponding shaft portion 14. Partial prosthesis portion 12 includes an enlarged head portion 16 having a substantially circular outer diameter and a rounded outer surface 18 for engaging the tympanic membrane. The rounded surfaces of head portion 16 of the illustrated embodiment minimize mechanical irritation of the tympanic membrane. Head portion 16 also includes a cannulated shaft portion 20 directly attached to head portion 16. In the illustrated embodiment, an aperture 22 through head portion 16 communicates with the hollow portion 24 of cannulated shaft portion 20. Aperture 22 is an optional feature which allows a physician to visualize the stapes during the implant procedure as well as providing a suitable point for gripping prosthesis 10 with the medical instruments being used. When only the malleus and incus portions of the middle ear require replacement, only partial prosthesis portion 12 is used. To provide for this function, the inside diameter of cannulated shaft 20 is adapted to slide over the head of the stapes.

When replacement of all three ossicles (malleus, incus and stapes) is necessary and a total prosthesis is required, shaft portion 14 is inserted into the hollow portion 24 of cannulated shaft portion 20 of partial prosthesis portion 12. In the illustrated embodiment, shaft portion 14 includes a first section 26 dimensioned to fit within the corresponding hollow portion 24 of shaft 20. Section 26 slides into the hollow portion 24 of partial prosthesis portion 12 until it abuts against surface 27, where in the preferred embodiment, it is held in place by mechanical friction. The illustrated shaft 14 also includes a portion 28 having a reduced diameter and a plate portion 30. Footplate portion 30 is adapted to be placed against the footplate of the stapes. The width of prosthesis footplate 30 is selected to approximately match the surface of the stapes footplate. The thickness of footplate 30 is selected such that a physician can trim (angle) the face of prosthesis footplate 30 to better match the surface of footplate of the stapes. The reduced diameter of portion 28 of shaft 14 allows easier fitting of prothesis 10 within the narrow bony opening of the middle ear near the stapes. Shaft portion 14 may be fabricated, in whole or in part, either a solid or hollow cylindrical shaft.

Shaft portion 14 may optionally include a notch 32 for engaging the malleus handle such that shaft portion 14 can be used by itself to bridge the gap between the malleus and the footplate of the stapes. Notch 32 may be formed by the physician using a scalpel or the like during surgery or may be added during manufacture.

Partial prosthesis portion 12 and shaft portion 14 may be made of any non-resorbable biocompatible or bioactive material. Preferred materials include bioactive ceramics/ polymer composites, hydroxyapatite, bioglass, porous polyethylene, porous polysulfon, silicon, teflon and metals such as titanium, platinum or stainless steel. Similarly, shaft portion 14 is made of a combination of these materials. In a preferred embodiment, head portion 16 may be fabricated from dense hydroxyapatite while shaft portion 20 and at least a portion of shaft 14 are made of flexible hydroxyapatite. The flexible hydroxyapatite is advantageous since it can be trimmed by the physician as required to customize prothesis 10 for a given patient. A description of flexible hydroxyapatite is given in the copending patent application Ser. No. 08/009,339 filed Jan. 26, 1993, and assigned to the assignee of the present application.

Although the present invention and its advantages have been described in detail, it should be understood that various changes, substitutions and alterations can be made herein without departing from the spirit and scope of the invention as defined by the appended claims.

What is claimed is:

1. A modular middle ear ossicles prosthesis for providing mechanical linkage between a tympanic membrane and an inner ear portion, such as a stapes or footprint of a stapes, the prosthesis comprising:

a first portion including an enlarged head having a substantially circular outer circumference and a rounded outer surface for engaging the tympanic membrane and a cannulated shaft extending from said head, said shaft having a predetermined length and defining a bore with an inside diameter sized to slide over a natural head of the stapes such that said first portion is operable alone as a partial ossicular prosthesis; and a second portion including an elongated shaft having a distal section sized to be inserted within said bore of the cannulated shaft of said first portion and a second section with a diameter smaller than a diameter of said distal section, resulting in a combination that is operable to provide a total ossicular prosthesis when replacement of all the ossicles is required.

2. The prothesis of claim 1 wherein said head includes an aperture therethrough, said aperture communicating with a hollow interior portion of said cannulated shaft.

3. The prosthesis of claim 1 wherein said second portion includes an oval shaped plate for engaging against the footplate of the stapes.

4. The prothesis of claim 1 wherein said head is constructed of a dense material and said cannulated shaft is constructed of a flexible material.

5. The prosthesis of claim 1 wherein at least a portion of said second portion is constructed of a flexible material.

6. A modular ossicular prosthesis for providing mechanical linkage in a middle ear between a tympanic membrane and an inner ear member, the prosthesis comprising:

a partial prosthesis comprising a dense enlarged head portion having a substantially circular outer circumference and a rounded outer surface for engaging the tympanic membrane, said head portion defining a through going aperture and a flexible shaft portion extending from said head portion, said shaft having a predetermined length and defining a throughgoing bore aligned and communicating with said aperture, said bore inside diameter being sized to slide over a natural head of a stapes; and a second assembly comprising an elongated flexible shaft having a first end sized to be inserted in said shaft portion bore of said partial prosthesis and an opposite end which includes a footplate for placement against the footplate of a stapes resulting in a combination that is operable to provide a total ossicular prosthesis when replacement of all the ossicles is required.

7. The ossicular prothesis of claim 6 wherein said partial prothesis is constructed of a biocompatible material.

8. The ossicular prothesis of claim 6 wherein said partial prothesis is constructed of a bioactive material.

9. The ossicular prothesis of claim 6 wherein said shaft of said second portion is constructed of a biocompatible material.

10. The ossicular prothesis of claim 6 wherein said shaft of said second portion is constructed of a bioactive material.

11. A modular universal middle ear prosthesis for providing mechanical linkage in a middle ear between a tympanic membrane and an inner ear portion, the prosthesis comprising:

a partial prosthesis comprising an enlarged head portion having a substantially circular outer circumference and a rounded outer surface for contacting the tympanic membrane and a tubular shaft extending from said head portion, said head portion defining an aperture communicating with a hollow portion of said tubular shaft and said shaft having a predetermined length and an inside diameter sized to slide over a natural head of a stapes; and a second shaft including a distal section of a first diameter sized to be inserted in said hollow portion of said tubular shaft of said partial prosthesis resulting in a combination of said partial prosthesis that is operable to provde a total ossicular prosthesis, said second shaft being provided with a second section which has a diameter that is amaller than said first diameter section.

12. The universal prothesis of claim 11 wherein said second shaft further includes a footplate extending radially from an end of said second section of said second shaft, said footplate adapted to be placed and engage a footplate of the stapes of the middle ear.

13. A modular universal middle ear prosthesis for providing mechanical linkage in a middle ear between a tympanic membrane and an inner ear portion, the prosthesis comprising:

a partial prosthesis comprising an enlarged head portion having a substantially circular outer circumference and a rounded outer surface for extending from said head portion, said head portion defining an aperture communicating with a hollow portion of said tubular shaft and said shaft being provided with an inside diameter sized to slide over a natural head of a stapes; and a second shaft having one end sized to be inserted in said hollow portion of said tubular shaft of said partial prosthesis and an opposing end provided with a footplate selected to substantially match the surface of a stapes footplate resulting in a combination that provides a total ossicular prosthesis.

* * * * *